(12) United States Patent
Sakairi et al.

(10) Patent No.: US 7,648,839 B2
(45) Date of Patent: Jan. 19, 2010

(54) METAL INDICATOR

(75) Inventors: Maria Sakairi, Toride (JP); Katsumi Yabusaki, Tsukuba (JP)

(73) Assignee: Kowa Co., Ltd., Nagoya-shi (JP)

( * ) Notice: Subject to any disclaimer, the term of this patent is extended or adjusted under 35 U.S.C. 154(b) by 341 days.

(21) Appl. No.: 11/631,096

(22) PCT Filed: Jun. 21, 2005

(86) PCT No.: PCT/JP2005/011318

§ 371 (c)(1),
(2), (4) Date: Dec. 28, 2006

(87) PCT Pub. No.: WO2006/001265

PCT Pub. Date: Jan. 5, 2006

(65) Prior Publication Data

US 2008/0057591 A1   Mar. 6, 2008

Related U.S. Application Data

(60) Provisional application No. 60/583,371, filed on Jun. 29, 2004.

(51) Int. Cl.
*G01N 33/20*   (2006.01)
(52) U.S. Cl. .......................... 436/80; 534/731
(58) Field of Classification Search ................ 436/80
See application file for complete search history.

(56) References Cited

FOREIGN PATENT DOCUMENTS

JP   2000-310628   11/2000

OTHER PUBLICATIONS

Denizli, Adil et al., "New Dye-Ligand: Procion Red MX-3B Carrying Poly (Egdma-Hema) Microbeads for Removal of Copper Ions", J.M.S-Pure Appl. Chem., vol. A35. No. 6, pp. 919-932, 1998.
Netpradit, Suchapa et al., "Adsorption of three azo reactive dyes by metal hydroxide sludge: effect of temperature, pH, and electrolytes", Journal of Colloid and Interface Science, vol. 270, pp. 255-261, 2004.

*Primary Examiner*—Yelena G Gakh
*Assistant Examiner*—Dirk Bass
(74) *Attorney, Agent, or Firm*—Oblon, Spivak, McClelland, Maier & Neustadt, L.L.P.

(57) ABSTRACT

To provide a novel copper ion indicator which is less influenced by interfering metal ions and which is useful for measurement of copper ion within a wide concentration range.

The invention provides a copper ion indicator containing a compound represented by formula (1):

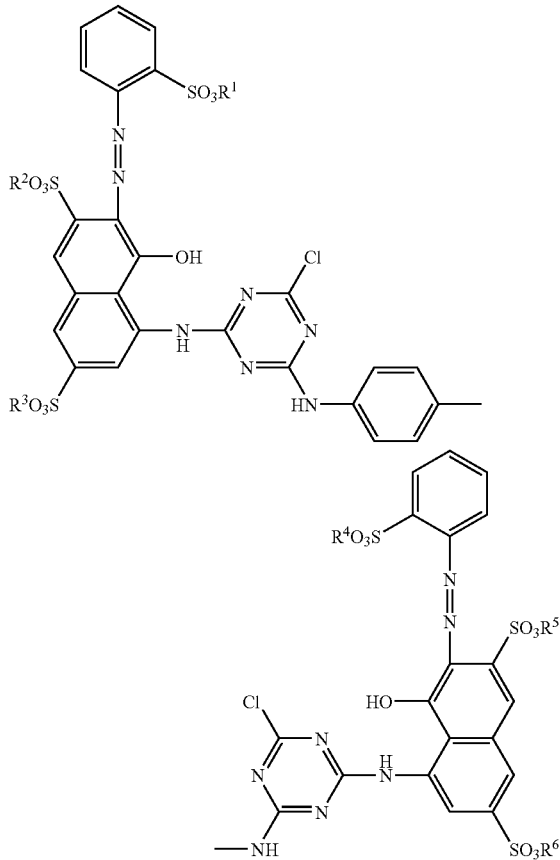

(1)

[wherein each of $R^1$, $R^2$, $R^3$, $R^4$, $R^5$, and $R^6$ represents a hydrogen atom or an alkali metal atom], and a method for determining copper ion concentration, which employs the indicator.

9 Claims, 2 Drawing Sheets

METAL INDICATOR

This application is a 371 of PCT/JP05/11318 filed Jun. 21, 2005, and claims benefit of U.S. provisional application Ser. No. 60/583,371, filed Jun. 29, 2004.

TECHNICAL FIELD

The present invention relates to a metal indicator for copper ions containing an azo dye.

BACKGROUND ART

In recent years, an increase in the amount of industrial wastes discharged from plants and facilities has become a striking social problem. Among such industrial wastes, waste liquid has a great impact upon the environment, because discharge volume thereof is huge. In conjunction with mounting concerns about environmental issues, effluent standards with respect to waste liquid containing heavy metals have become more rigorous. Under such circumstances, in order to evaluate the potential hazard of waste liquid, there is demand for a simple method for determining heavy metal concentration of waste liquid with high sensitivity.

Among heavy metal species contained in waste liquid, copper is eluted from copper pipes and brass parts employed for water supply equipment or for transportation of mine wastewater, industrial wastewater, etc., and is present as a copper sulfate or copper chloride to be used as an organism inhibitor; and long-term drinking of water containing a high level of copper resulted from above factors as well as pesticide contamination is known to make the skin and hair greenish and to cause other conditions.

One typical method for determining heavy metal in waste liquid is measuring absorbance of each target element—metal indicator complex. A variety of metal indicators each having a specificity for a target element is known in the art.

Meanwhile, azo compounds having a substituent such as an amino group, a hydroxyl group, or a sulfonate group have been employed as dyes. Some azo dyes form a complex with a metal ion with change in color of the corresponding free dyes. Hitherto, a variety of metal indicators exhibiting such color change have been employed.

Examples of the azo compounds generally employed as a metal indicator for copper ions (hereinafter referred to as copper ion indicator) include 2-(5-bromo-2-pyridylazo)-5-[N-(n-propyl)-N-(3-sulfopropyl)amino]phenol disodium salt dihydrate (5Br.PAPS, product of Dojindo Laboratories), 2-[1-(2-hydroxy-5-sulfophenyl)-3-phenyl-5-formazano] benzoic acid sodium salt (Zincon, product of Dojindo Laboratories), 1-(2-pyridylazo)-2-naphthol (PAN, product of Dojindo Laboratories), a reagent (mixture of PAN and Cu-EDTA, Cu-PAN, product of Dojindo Laboratories), 2-(5-bromo-2-pyridylazo)-5-[N-(n-propyl)-N-(3-sulfopropyl) amino]aniline sodium salt (5Br.PSAA, product of Dojindo Laboratories), and 4-(2-pyridylazo)resorcinol (PAR, product of Dojindo Laboratories) (Patent Document 1).

Patent Document 1: Japanese Patent Application Laid-Open (kokai) No. 2000-338096

DISCLOSURE OF THE INVENTION

Problems to be Solved by the Invention

However, these copper ion indicators have drawbacks. The indicators have a narrow measurable concentration range with respect to samples such as waste liquid which possibly have a wide heavy metal concentration range. In the case where a sample such as waste liquid containing large amounts of interfering metal ions, the range within which copper ion concentration can be determined is limited. In this case, for example, interfering metal ions must be sequestered (e.g., chelated or masked).

Thus, an object of the present invention is to provide a novel copper ion indicator which is less influenced by interfering metal ions, and which is useful for measurement of copper ion within a wide concentration range.

Means for Solving the Problems

The present inventors have carried out extensive studies, and have found that a compound which is generally known as azo dye and which is represented by formula (1) is a useful copper ion indicator which is useful for measurement of copper ion within a wide concentration range and which is less influenced by interfering metal ions. The present invention has been accomplished on the basis of this finding. Patent Document 1: Japanese Patent Application Laid-Open Accordingly, the present invention provides a copper ion indicator containing a compound represented by formula (1):

[F1]

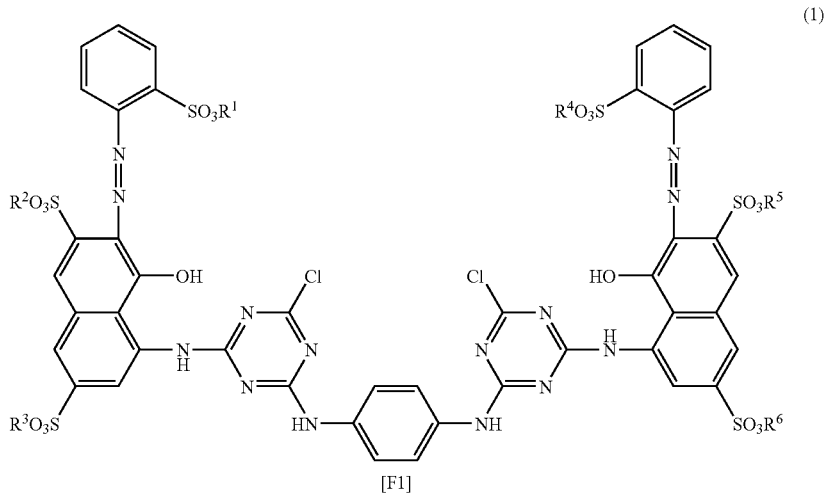

(1)

[F1]

[wherein each of $R^1$, $R^2$, $R^3$, $R^4$, $R^5$, and $R^6$ represents a hydrogen atom or an alkali metal atom].

The present invention also provides a method for determining copper ion concentration by use of the copper ion indicator.

EFFECTS OF THE INVENTION

The metal indicator of the present invention is useful for measurement of copper ion within a wide concentration range and is less influenced by interfering metal ions. Therefore, the metal indicator is useful for the determination of copper ion concentration of waste liquid or other samples.

MODES FOR CARRYING OUT THE INVENTION

Figure 1:
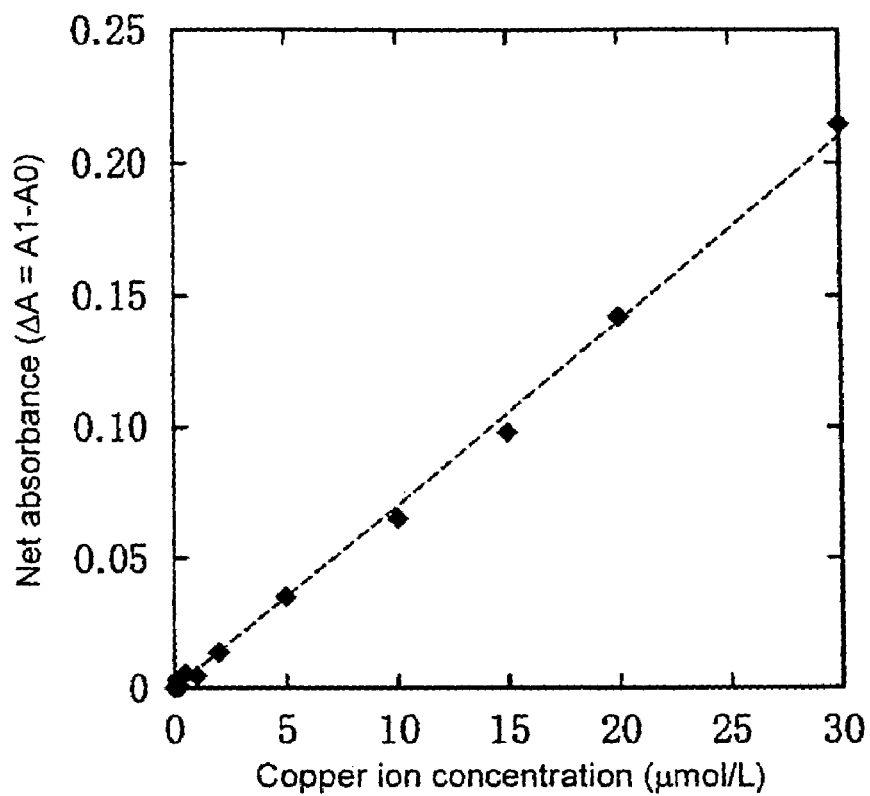
FIG. 1 is a graph showing the results of copper ion concentration determination obtained by use of an aqueous RR120 solution.

The compound represented by formula (1) in a metal indicator of the present invention forms a complex specifically with copper ion contained in a sample. In formula (1), at least one of $R^1$, $R^2$, $R^3$, $R^4$, $R^5$, and $R^6$ is preferably an alkali metal atom, more preferably lithium, sodium, or potassium, particularly preferably sodium. Among the compounds represented by formula (1), a tetrasodium salt ($R^1=R^4=H$, $R^2=R^3=R^5=R^6=Na$) is available as Reactive Red 120 (RR120), which is a product of Sigma-Aldrich Corporation.

The metal indicator of the present invention may be employed in the form of a solution which is prepared by dissolving a compound represented by formula (1) directly in a buffer or a similar medium. The concentration of the formula (1) compound is 0.1 to 1,000 μmol/L, preferably 10 to 200 μmol/L. In the case of determination of a low copper ion concentration (0 to 30 μmol/L), the formula (1) compound concentration is particularly preferably 30 μmol/L, whereas in the case of determination of a high copper ion concentration (20 to 200 μmol/L), the formula (1) compound concentration is particularly preferably 200 μmol/L.

Alternatively, the metal indicator of the present invention may also be employed in the form of metal indicator paper, which is prepared by chemically bonding a compound represented by formula (1) to a sheet-like support made of a transparent or non-transparent cellulose material (i.e., a dying process). In use, the metal indicator paper is immersed in an aqueous solution containing copper ions and an additive such as a buffer.

The above metal indicator paper may be readily produced through, for example, immersing a sheet-like support made of a transparent or non-transparent cellulose material in a dye solution at room temperature or under heating. Examples of the transparent cellulose material forming the sheet-like support include cellophane and cellulose gel. Examples of the sheet-like support made of non-transparent cellulose material include filter paper, cotton ground fabric, and non-woven fabric. The sheet-like support is preferably made of a transparent cellulose material, with cellophane being particularly preferred. In the case where a sheet-like support is dyed, the formula (1) compound solution (hereinafter may also be referred to as dye solution) preferably has a concentration of 0.01 to 50 mass %, particularly preferably 0.01 to 10 mass %. The immersion temperature is preferably 25 to 90° C., particularly preferably 50 to 85° C.

The dying degree of the sheet-like support colored by the aforementioned dye is represented by light transmittance or light reflectance. When a sheet-like support made of a transparent cellulose material is dyed, light transmittance (transmitted light intensity)/(incident light intensity)×100%) at, for example, 595 nm is 1 to 98%, preferably 10 to 80%. When a sheet-like support made of a non-transparent cellulose material is dyed, light transmittance (transmitted light intensity)/(incident light intensity)×100%) at, for example, 543 nm is 1 to 98%, preferably 10 to 80%.

No particular limitation is imposed on the type of the buffer, and examples of the buffer include a phosphate buffer, a phthalate buffer, a citrate buffer, Tris, a maleate buffer, a succinate buffer, an oxalate buffer, a tartrate buffer, an acetate buffer, a borate buffer, and Good's buffer. No particular limitation is imposed on the buffer concentration. The buffer concentration is preferably 0.001 to 200 mmol/L, particularly preferably 0.1 to 100 mmol/L. The pH of the metal indicator of the present invention may be adjusted by use of the buffer, and is generally 2 to 8, preferably 3 to 7, more preferably 5 to 6, particularly preferably about 5.5.

To the metal indicator of the present invention, an optional component generally employed in determination of heavy metal ion concentration of a sample may be arbitrarily added, so long as the effects of the present invention are not impaired. Examples of such optional components include a surfactant, a chelating agent, and a masking agent. Examples of the surfactant include cationic surfactants, anionic surfactants, and nonionic surfactants. Examples of the chelating agent and masking agent include polyethyleneimine, citric acid, ethylenediaminetetraacetic acid (EDTA), and ethylene glycol tetraacetic acid (EGTA).

No particular limitation is imposed on the sample to which the metal indicator of the present invention can be applied, so long as the sample contains copper ions. Examples of the sample include mine wastewater and industrial wastewater. The sample may be subjected to analysis as is. Alternatively, the sample may be subjected to filtration or dialysis before analysis. If required, the sample may be concentrated or diluted. By use of the metal indicator of the present invention, a copper ion concentration of a sample of about 1,000 μmol/L or less can be determined without any problems. However, the concentration to be determined is preferably 0 to 100 μmol/L, more preferably 0 to 50 μmol/L, particularly preferably 0 to 30 μmol/L.

The determination of copper ion concentration by use of the metal indicator of the present invention is preferably performed through the absorbance method. In the case where a sheet-like support made of a non-transparent cellulose material is used, the change in color of the dye caused by absorption of a copper ion is preferably derived from reflectance of the incident light reflected by the sheet-like support. In the case where a sheet-like support made of a transparent cellulose material is used, the dye color change is preferably derived from absorbance of the incident light absorbed by the sheet-like support.

When a low-range copper ion concentration is determined, the absorption wavelength is 520 to 560 nm, preferably 530 to 550 nm, particularly preferably 543 nm, whereas when a high-range copper ion concentration is determined, the absorption wavelength is 570 to 620 nm, preferably 580 to 610 nm, particularly preferably 595 nm. The sample solution is determined generally at 0 to 100° C., preferably at 15 to 60° C., particularly preferably at about 25° C.

EXAMPLES

The present invention will next be described in detail by way of examples, which should not be construed as limiting the invention thereto.

Example 1

RR 120 (product of Sigma-Aldrich Corporation) was dissolved in a 100-mmol/L acetate buffer (pH: 5.5), to thereby prepare a dye solution having a concentration of 110 μmol/L. The dye solution (990 μL) was mixed with a copper-ion-containing sample (concentration 0, 5, 10, 15, 20, or 30 μmol/L) (10 μL). Absorbance (at 595 nm) of a mixture of the dye solution and a copper-ion-free sample (i.e., water) (10 μL) (A0) and absorbance (at 595 nm) of a mixture of the dye solution and each sample containing copper ions (A1) were measured by means of a Beckman spectrophotometer (type DU640), and net absorbance ($\Delta A = A1 - A0$) corresponding to the copper ion concentration of each sample (final concentration, after dilution) was calculated.

FIG. 1 shows the results.

Example 2

(1) Fabrication of Metal Indicator Paper

A cellophane sheet (thickness: 0.1 mm) was immersed in a 0.01-mass % aqueous solution of RR 120 (product of Sigma-Aldrich Corporation), followed by heating at 60° C. for 10 minutes. Subsequently, $Na_2SO_4 \cdot 10H_2O$ was added to the solution so that the final concentration was adjusted to 7 mass %, followed by heating at 80° C. for 20 minutes for allowing the system to react. Subsequently, $Na_3PO_3$ was added to the solution so that the final concentration was adjusted to 1.5 mass %, followed by heating at 80° C. for 30 minutes for fixing the dye onto the cellophane sheet. In order to remove unreacted dye, the sheet was thoroughly washed with water and boiled in a 0.2-mass % Tween20 (product of Sigma-Aldrich Corporation). The thus-treated cellophane sheet was thoroughly washed with water, and dried, to thereby yield a cellophane sheet dyed with RR 120.

(2) Copper Ion Concentration Determination

The metal indicator paper produced in (1) above was immersed in a solution prepared by mixing a 100-mmol/L acetate buffer (pH: 5.5) (990 μL) with each of sample solutions having a copper ion concentration of (0, 25, or 50 μmol/L) (10 μL), and the system was allowed to react at 25° C. for 10 minutes. Absorbance (at 595 nm) (A1) of the thus-treated cellophane sheet was measured. Separately, a cellophane sheet was immersed in a sample prepared by mixing a copper-ion-free sample (i.e., water) (10 μL) and an acetate buffer (990 μL), followed by reaction at 25° C. for 10 minutes. Absorbance (at 595 nm) (A0) of the thus-treated cellophane sheet was measured.

Figure 2:
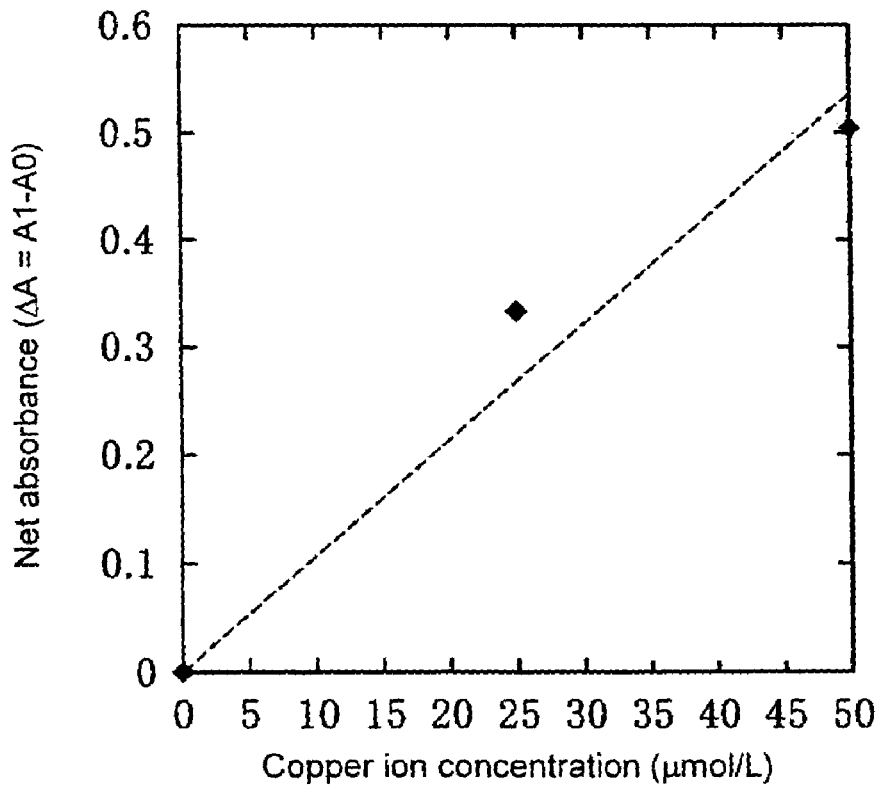
FIG. 2 is a graph showing the results of copper ion concentration determination obtained by use of a metal indicator paper.

FIG. 2 shows the results. In the graph, the Y-axis represents net absorbance ($\Delta A = A1 - A0$) corresponding to the copper ion concentration of each sample (final concentration, after dilution).

As is clear from FIGS. 1 and 2, net absorbance (difference in absorbance) increased in proportion to copper ion concentration, indicating a good quantitative relationship between the two properties. Therefore, use of the metal indicator of the present invention was found to attain determination of copper ion concentration within a wide concentration range of 0 to 50 μmol/L at high sensitivity.

Example 3

Effect of Concomitant Metal Ions 1

RR 120 (product of Sigma-Aldrich Corporation) was dissolved in a 100-mmol/L acetate buffer (pH: 5.5), to thereby prepare a dye solution having a concentration of 30 μmol/L. The dye solution (990 μL) was mixed with an aqueous solution (10 μL) having a copper ion concentration of 5 μmol/L and containing no other interfering ions. Absorbance (at 543 nm) (B0) of the mixture was measured. The above dye solution (990 μL) was mixed with each of samples (10 μL) having a copper ion concentration of 5 μmol/L and containing calcium ions, cadmium ions, or cobalt ions at a concentration of 5 to 20 μmol/L. Absorbance (at 543 nm) (B1) of each mixture was measured. Through these experiments, effects of concomitant metal ions were investigated. In addition to RR 120, effects of concomitant metal ions on conventional reagents for copper ion determination; 5Br.PSAA (50 μmol/L), 5Br.PAPS (50 μmol/L), and Stilbazo (70 μmol/L), were investigated in a similar manner.

Figure 3:
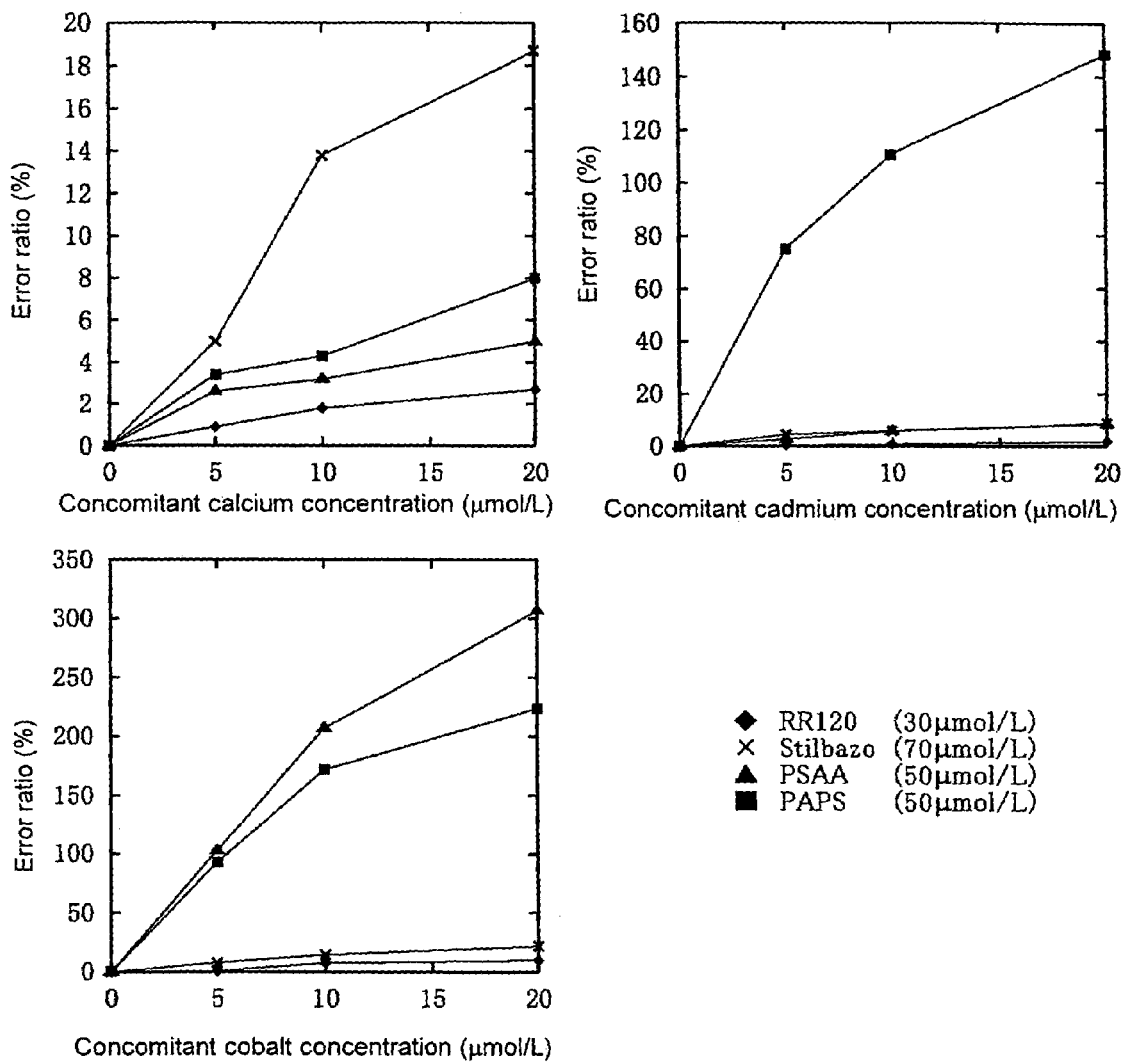
FIG. 3 gives graphs showing effects of concomitant metal ions on copper ion concentration measurements.

FIG. 3 shows the results. The Y-axis represents error ratio: (|B0−B1|/B0)×100(%) (|B0−B1|; absolute value of B0−B1).

5Br.PSAA: 2-(5-bromo-2-pyridylazo)-5-(N-(n-propyl)-N-(3-sulfopropyl)amino)aniline sodium salt (product of Dojindo Laboratories)

5Br.PAPS: 2-(5-bromo-2-pyridylazo)-5-(N-(n-propyl)-N-(3-sulfopropyl)amino]phenol disodium salt dihydrate (product of Dojindo Laboratories)

Stilbazo: 4,4'-bis(3,4-dihydroxyphenylazo)-2,2'-stilbenedisulfonic acid diammonium salt (product of Dojindo Laboratories)

Example 4

Effect of Concomitant Metal Ions 2

The procedure of Example 3 was repeated, except that samples containing a 5-μmol/L nickel ions, lead ions, or sodium ions as concomitant metal ions were analyzed, whereby effects of concomitant metal ions were investigated.

Table 1 shows the results. The numerical data in Table 1 are measurement error ratios (%).

TABLE 1

| | Concomitant metal ions (5 μmol/L) | | |
|---|---|---|---|
| Dye (concentration) | Ni | Pb | Na |
| 5Br•PSAA (50 μmol/L) | 0.9 | 3.1 | 1.9 |
| 5Br•PAPS (50 μmol/L) | 38.3 | 44.5 | 2.5 |
| Stilbazo (70 μmol/L) | 13.5 | 10.5 | 0.6 |
| RR 120 (30 μmol/L) | 0.2 | 0.6 | 3.6 |

As is clear from FIG. 3 and Table 1, the metal indicator of the present invention is less affected by concomitant ions (calcium ions, cadmium ions, cobalt ions, nickel ions, lead ions, and sodium ions).

The invention claimed is:

1. A method for determining copper ion concentration in a sample containing a copper ion, comprising reacting the sample with a copper ion indicator composition comprising a compound represented by formula (1):

[F1]

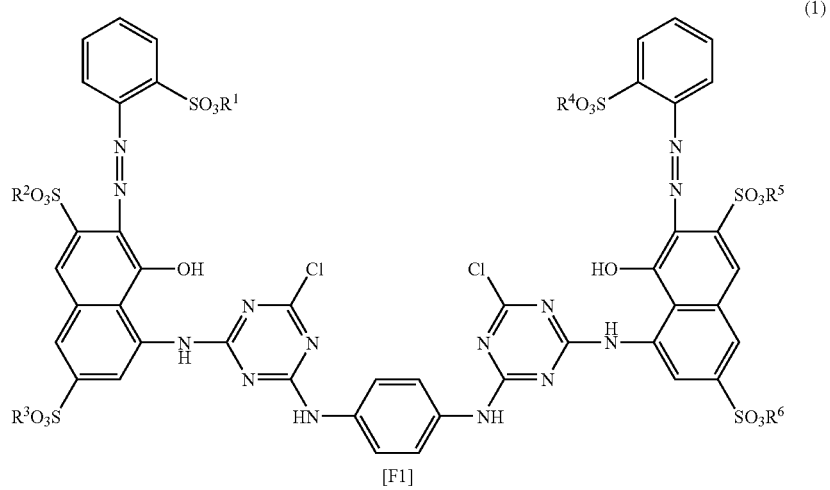

wherein each of $R^1$, $R^2$, $R^3$, $R^4$, $R^5$, and $R^6$ represents a hydrogen atom or an alkali metal atom; and measuring a change in absorbance of the indicator composition.

2. The method according to claim 1, wherein the indicator composition is a buffer comprising a compound represented by formula (1) at a concentration of 0.1 to 1,000 μmol/L.

3. The method according to claim 1, wherein the indicator is indicator paper comprising a compound represented by formula (1) chemically bonded to a sheet-like support made of a transparent or non-transparent cellulose material.

4. The method according to claim 1, wherein the copper ion concentration in the sample is 1,000 μmol/L or less.

5. The method according to claim 1, wherein the copper ion indicator composition comprises a compound represented by formula (1) wherein $R^1$=$R^4$=H and $R^2$=$R^3$=$R^5$=$R^6$=Na.

6. The method according to claim 1, wherein the change in absorbance of the indicator composition is determined at a wavelength of 520 to 560 nm.

7. The method according to claim 1, wherein the change in absorbance of the indicator composition is determined at a wavelength of 530 to 550 nm.

8. The method according to claim 1, wherein the change in absorbance of the indicator composition is determined at a wavelength of 570 to 620 nm.

9. The method according to claim 1, wherein the change in absorbance of the indicator composition is determined at a wavelength of 580 to 610 nm.

* * * * *